United States Patent [19]
Johnston et al.

[11] Patent Number: 5,599,334
[45] Date of Patent: Feb. 4, 1997

[54] ABSORBENT ARTICLE WITH SUBSTANTIAL VOLUME CAPACITY AND RETAINABLE SHAPE

[75] Inventors: Lee W. Johnston, Downingtown; Timothy A. Smith, Sanatoga; Carol A. Gephart, Spring City; Mary E. Doucette, East Lansdowne; Louis P. Bove, Trappe, all of Pa.

[73] Assignee: Confab, Inc., King of Prussia, Pa.

[21] Appl. No.: 151,385

[22] Filed: Nov. 12, 1993

(Under 37 CFR 1.47)

[51] Int. Cl.⁶ ..................................... A61F 13/15
[52] U.S. Cl. ..................... 604/368; 604/359; 604/365; 604/369; 604/380; 604/385.1; 604/385.2; 604/387
[58] Field of Search .................... 604/359, 365, 604/366, 368, 369, 378–380, 385.1–387

[56] References Cited

U.S. PATENT DOCUMENTS

| | | |
|---|---|---|
| Re. 33,106 | 11/1989 | Beckestrom . |
| 2,331,271 | 10/1943 | Gilchrist . |
| 3,639,917 | 2/1972 | Althouse . |
| 3,805,790 | 4/1974 | Kaczmarzyk et al. . |
| 3,819,401 | 6/1974 | Massengale et al. . |
| 3,848,599 | 11/1974 | Schaar . |
| 3,912,565 | 10/1975 | Koch et al. . |
| 3,916,900 | 11/1978 | Breyer et al. ................. 604/369 |
| 3,954,107 | 5/1976 | Chesky et al. . |
| 4,014,341 | 3/1977 | Karami . |
| 4,041,951 | 8/1977 | Sanford . |
| 4,166,464 | 9/1979 | Korpman . |
| 4,184,902 | 1/1980 | Karami . |
| 4,226,238 | 10/1980 | Bianco . |
| 4,259,220 | 3/1981 | Bunnelle et al. . |
| 4,261,782 | 4/1981 | Teed . |
| 4,300,562 | 11/1981 | Pieniak . |
| 4,309,236 | 1/1982 | Teed . |
| 4,323,068 | 4/1982 | Aziz . |
| 4,324,245 | 4/1982 | Mesek et al. . |
| 4,324,246 | 4/1982 | Mullane et al. . |
| 4,326,528 | 4/1982 | Ryan et al. . |
| 4,337,771 | 7/1982 | Pieniak et al. . |
| 4,341,217 | 7/1982 | Ferguson et al. . |
| 4,352,355 | 10/1982 | Mesek et al. . |
| 4,357,938 | 11/1982 | Ito et al. . |
| 4,360,021 | 11/1982 | Stima . |
| 4,372,312 | 2/1983 | Fendler et al. . |
| 4,407,284 | 10/1983 | Pieniak . |
| 4,490,147 | 12/1984 | Pierce et al. . |
| 4,490,148 | 12/1984 | Beckestrom . |
| 4,535,020 | 8/1985 | Thomas et al. . |
| 4,556,596 | 12/1985 | Meuli . |
| 4,573,991 | 3/1986 | Pieniak et al. . |
| 4,579,556 | 4/1986 | McFarland . |
| 4,597,761 | 7/1986 | Buell . |
| 4,629,643 | 12/1986 | Curro et al. . |
| 4,634,440 | 1/1987 | Widlund et al. . |
| 4,636,209 | 1/1987 | Lassen . |
| 4,637,819 | 1/1987 | Ouellette et al. . |
| 4,668,230 | 5/1987 | Damico et al. . |

(List continued on next page.)

FOREIGN PATENT DOCUMENTS

| | | |
|---|---|---|
| 0091412A2 | 10/1983 | European Pat. Off. . |
| 0320991A2 | 6/1989 | European Pat. Off. . |
| 0335253A1 | 10/1989 | European Pat. Off. . |
| 0359501A2 | 3/1990 | European Pat. Off. . |
| 0442223A1 | 8/1991 | European Pat. Off. . |
| 0572033A2 | 12/1993 | European Pat. Off. . |

*Primary Examiner*—John G. Weiss
*Assistant Examiner*—K. M. Reichle
*Attorney, Agent, or Firm*—Finnegan, Henderson, Farabow, Garrett & Dunner, L.L.P.

[57] ABSTRACT

An absorbent article having a substantial volume capacity and retainable shape is disclosed which includes a cover sheet, an absorbent core, and a multi-layered moisture barrier laminate including a polymeric foam layer and at least one thermally bonded layer. Also, elastic members are attached to longitudinal sides of the article to form a cup-shaped article which has a cupping strength of about 30 grams to about 90 grams.

20 Claims, 3 Drawing Sheets

U.S. PATENT DOCUMENTS

| | | |
|---|---|---|
| 4,673,402 | 6/1987 | Weisman et al. . |
| 4,681,793 | 7/1987 | Linman et al. . |
| 4,685,914 | 8/1987 | Holtman . |
| 4,690,679 | 9/1987 | Mattingly, III et al. . |
| 4,699,823 | 10/1987 | Kellenberger et al. . |
| 4,701,177 | 10/1987 | Ellis et al. . |
| 4,710,186 | 12/1987 | DeRossett et al. . |
| 4,753,644 | 6/1988 | Cottenden et al. . |
| 4,753,645 | 6/1988 | Johnson . |
| 4,755,413 | 7/1988 | Morris . |
| 4,762,521 | 8/1988 | Roessler et al. . |
| 4,770,657 | 9/1988 | Ellis et al. . |
| 4,772,282 | 9/1988 | Oakley . |
| 4,781,962 | 11/1988 | Zamarripa et al. . |
| 4,798,603 | 1/1989 | Meyer et al. . |
| 4,820,294 | 4/1989 | Morris . |
| 4,840,692 | 6/1989 | Kamstrup-Larsen . |
| 4,846,813 | 7/1989 | Raley . |
| 4,886,512 | 12/1989 | Damico et al. . |
| 4,897,084 | 1/1990 | Ternstrom et al. . |
| 4,908,026 | 3/1990 | Sukiennik et al. . |
| 4,911,701 | 3/1990 | Mavinkurve . |
| 4,940,462 | 7/1990 | Salerno . |
| 4,944,735 | 7/1990 | Mokry . |
| 5,006,394 | 4/1991 | Baird . |
| 5,009,653 | 4/1991 | Osborn, III . |
| 5,013,309 | 5/1991 | Baigas, Jr. et al. . |
| 5,019,062 | 5/1991 | Ryan et al. . |
| 5,023,124 | 6/1991 | Kobayashi . |
| 5,026,589 | 6/1991 | Schechtman . |
| 5,032,121 | 7/1991 | Mokry ................................ 604/385.2 |
| 5,061,259 | 10/1991 | Goldman et al. . |
| 5,074,856 | 12/1991 | Coe et al. . |
| 5,080,658 | 1/1992 | Igaue et al. . |
| 5,128,187 | 7/1992 | Polski . |
| 5,129,893 | 7/1992 | Thoren ................................ 604/385.2 |
| 5,141,794 | 8/1992 | Arroyo . |
| 5,151,091 | 9/1992 | Glaug et al. . |
| 5,167,654 | 12/1992 | Yang . |
| 5,171,238 | 12/1992 | Kajander . |
| 5,181,563 | 1/1993 | Amaral . |
| 5,188,624 | 2/1993 | Young, Sr. et al. . |
| 5,188,625 | 2/1993 | Van Iten et al. . |
| 5,197,959 | 3/1993 | Buell ........................................ 604/378 |
| 5,217,445 | 6/1993 | Young et al. . |
| 5,234,422 | 8/1993 | Sneller et al. . |
| 5,401,266 | 3/1995 | Runeman et al. ................... 604/385.2 |

ABSORBENT ARTICLE WITH SUBSTANTIAL VOLUME CAPACITY AND RETAINABLE SHAPE

BACKGROUND OF THE INVENTION

The present invention relates to an absorbent article, and more particularly, an incontinence article, which holds a substantial volume of fluid and has a retainable shape.

Adult diapers are now commercially available with capacities to hold as much as 1,200 ml of fluid. Important advances have also been made in the fit, comfort, closure, quietness, and rewet (surface dryness) of diapers. In spite of these advances, diapers designed for adult incontinence still present problems to users, particularly those who are ambulatory. For example, the fluffy absorbent component, e.g., cellulose pulp fibers, tends to shift and form uneven distributions and clumps. Due to the size and bulkiness of these diapers, wearers tend to be hot, uncomfortable, and concerned about the diaper showing through their garments.

In addition, when away from home, the disposal of diapers presents a problem. Similarly, transporting and storing extra diapers may be an inconvenience.

It is therefore not surprising that there is interest in developing smaller, thinner, more compact articles, e.g., those that can be adhesively attached to undergarments as with sanitary napkins.

Hydrogel forming polymers are of interest in this development, in part, possibly due to the polymers' capacity to absorb 25–35 times their weight in fluid (at least twice the rate of pulp fiber). These polymers, combined in granular form with cellulose pulp structures, are of interest in providing essential technology to achieve sufficient volume capacity in the down-scaling of the size and weight of absorbent articles. Such hydrogel forming polymers are described in detail in Brandt et al, U.S. Pat. No. Re. 32,649. They are often referred to as superabsorbent polymers (SAP).

There are several well known processes for incorporating these hydrogel forming particles into an absorbent material:

1) Direct dry mixing with airborne cellulose pulp in, e.g. fluff forming chambers.

2) Direct application to the surface of various nonwoven fibrous materials or paper.

3) Bonding of SAP granules between two layers of nonwoven material or paper.

4) In-line application of SAP concomitantly with a latex used to bind nonwoven fibers as for example in Makoui, U.S. Pat. No. 5,128,082.

A second challenge in the design of a relatively small, thin, and compact adult incontinence article is the need to rapidly capture and absorb fluid. Pads having absorbent cores which are a combination of a fluid pervious material, cellulose pulp fluff, SAP, and a binder covered with a thin lightweight cover sheet, such as a thermally bonded web of polypropylene staple fibers and backed with an impervious film at 1–3 mil. thickness having an overall length of about 9–10 inches and an overall width of 4–5 inches do not always provide adequate protection, e.g., when the entire bladder is voided since an appreciable quantity of fluid may tend to run off the sides. Such absorbent articles do not provide sufficient drainage, especially in the Z-direction of the device to quickly capture fluids.

In the control of fluids using relatively small, thin, compact articles, a third element of performance is related to the distribution of fluid among the various layers of material which form the overall product. This property contributes importantly to the user's feeling of comfort, dryness, and overall security. More specifically, it is highly desirable that a pad be designed to contain and hold fluids well within the absorbent core even when subjected to the weight of the user.

SUMMARY OF THE INVENTION

It is therefore an object of the present invention to provide a relatively small, thin, and compact absorbent article for the absorption and control of a body fluid such as urine associated with ambulatory incontinence with particular emphasis on the product retaining its shape, thus allowing the fluid to flow and be maintained within the product and away from the body of the wearer. Also, when the pad keeps its original shape, the user feels more confident by being aware of the edges of the product and the volume capacity thereof.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purposes of the present invention, as embodied and broadly described herein, the present invention relates to an absorbent cup-shaped article comprising a fluid pervious cover sheet which is preferably a nonwoven material. Adjacent the cover sheet is an absorbent core having a garment-facing surface and a body-facing surface which is preferably a contoured pulp fluff pad permeated with a superabsorbent polymer. Adjacent the garment-facing surface of the absorbent core is a multi-layered moisture barrier laminate comprised of a polymeric foam layer and at least one thermally bonded layer, preferably of a nonwoven material which is preferably carded. The laminate is positioned so that the foam layer faces the garment-facing surface of the absorbent core. The laminate has a flexural resistance of from about 16 grams to about 106 grams. The article also has elastic means attached to longitudinal sides thereof to form the cup-shaped article which has a cupping strength of from about 30 grams to about 90 grams. Optionally, a tissue layer can be placed between the cover sheet and on the body-facing surface of the absorbent core.

It is to be understood that both the foregoing general description and the following detailed description are exemplary and explanatory only and are not restrictive of the present invention, as claimed.

DETAILED DESCRIPTION OF THE INVENTION

Figure 1:
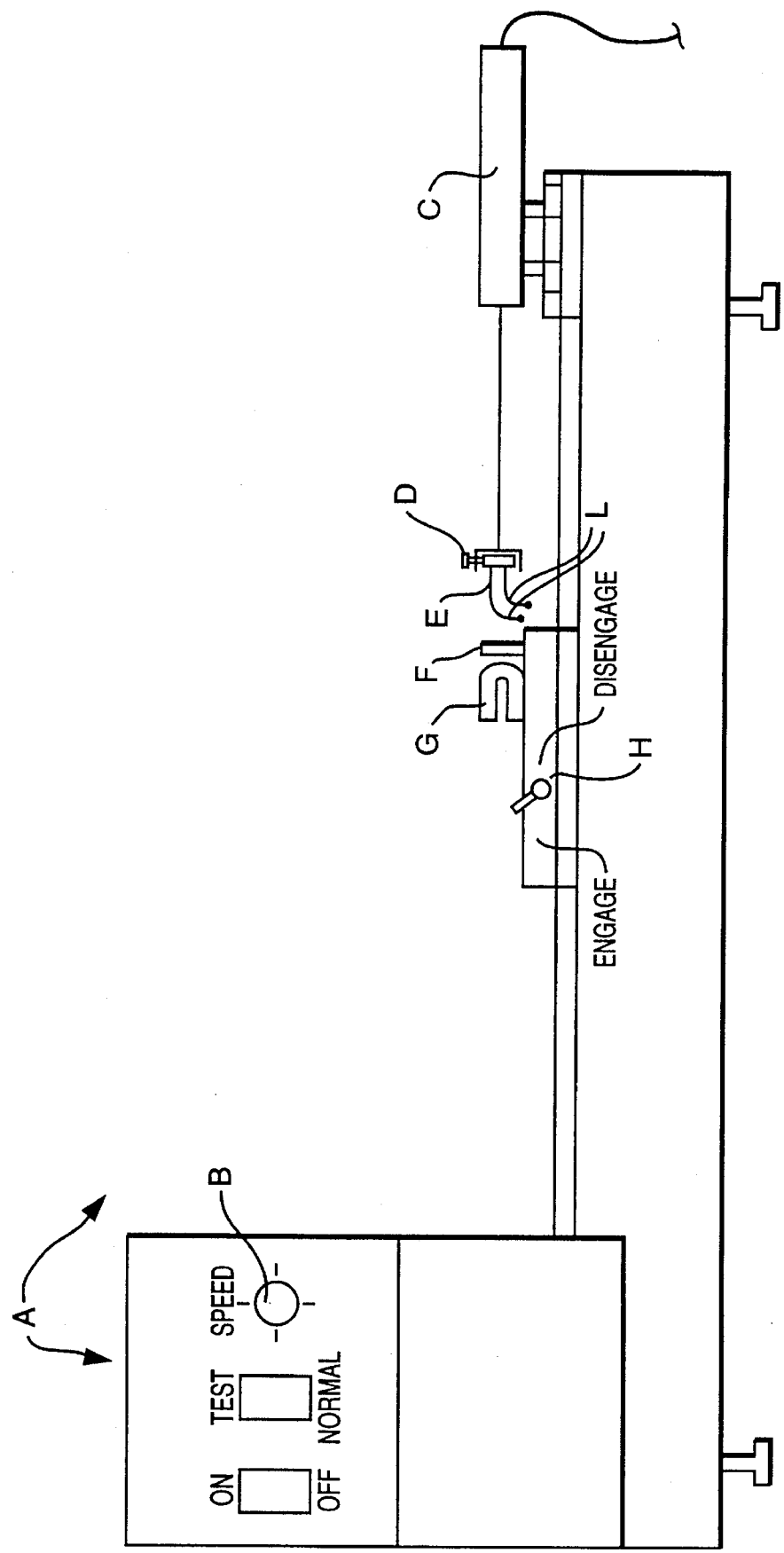
FIG. 1 is a view of equipment for measuring the cupping strength of an absorbent article.

As used herein, the term "absorbent article" refers to an article which absorbs and contains body exudates, and, more specifically, refers to an article which is placed against or in proximity to the body of the wearer to absorb and contain the various exudates discharged from the body. Further, the term "disposable" is used herein to describe an absorbent article which is not intended to be laundered or otherwise restored or reused as an absorbent article. In other words, the disposable article is intended to be discarded after a single use, and, preferably, composted or otherwise disposed of for recycling in an environmentally compatible manner.

The absorbent core of the present invention may be of any absorbent material which is capable of absorbing or retaining a liquid such as urine, feces, and menses. The absorbent core has a garment-facing surface and a body-facing surface. Preferably, the absorbent core is a contoured pulp fluff pad which is permeated with a superabsorbent polymer. More preferably, this contoured pulp fluff pad (M) (FIG. 2) is embossed (e.g. diamond-shaped) and the SAP, in granular form, is uniformly permeated throughout the contoured pulp fluff pad. The amount of SAP preferably permeated into the fluff is from about 3 to about 8 grams, most preferably from about 5 to about 6 grams. Also, the SAP granule size preferably is such that about 15% to about 25% by weight is retained on 30 mesh, most preferably about 19% by weight, and from about 50% to about 60% by weight is retained on 50 mesh, most preferably about 55%. With respect to the contoured pulp fluff pad, as an example, in a dumbbell shaped absorbent article having a length of about 250 mm to about 300 mm, from about 10 grams to about 20 grams pulp fluff can be used, preferably from about 13.5 grams to about 15.5 thereof.

The absorbent core may be manufactured in a wide variety of sizes and shapes, for example, rectangular, oval, hour glass, dog bone, asymmetric, and dumbbell. Further, a wide variety of liquid-absorbent materials may be used as part of the absorbent core such as comminuted wood pulp which is generally referred to as air felt, creped cellulose wadding, melt blown polymers including co-form, cross-linked chemically modified cellulosic fibers, synthetic fibers, tissue including tissue wraps and tissue laminates, absorbent foams, absorbent sponges, absorbent jelling materials, or any equivalent material, combination of materials, or mixtures of these.

The configuration and construction of the absorbent core may also be varied. For instance, the absorbent core may have varying caliper zones, hydrophilic gradients, super absorbent gradients, or low density and lower average basic weight acquisition zones. Also, the absorbent core may comprise one or more layers or structures. The total absorbent capacity of the absorbent core should be compatible with the design loading and the intended use of the absorbent device. Furthermore, the size and absorbent capacity of the absorbent core may be varied to accommodate different uses such as incontinence pads, panty liners, regular sanitary napkins, or overnight sanitary napkins.

Optionally, the absorbent core can also contain an odor neutralizer. Preferably, the odor neutralizer is in the form of a fluid that is applied in spray form to the absorbent core during manufacturing. Preferably, from about 0.10 gram to about 0.5 gram of fluid is applied to the absorbent core. Commercially available odor neutralizer fluids which can be used in the present invention include masking fragrances, zeolites, baking soda, and charcoal. A preferred odor neutralizer can be obtained from International Aromatics of North Bergen, N.J.

On one surface of the absorbent core (i.e., on the body-facing surface of the absorbent core), a tissue layer can be placed which aids in the transfer of fluid away from the body. Preferably, this tissue layer is a nonwoven material which has a basis weight of from about 15 to 25 gm/m$^2$, most preferably about 20 gm/m$^2$. Also, preferably the tissue layer (N) (FIG. 2) extends the entire length of the absorbent core and is preferably narrower in width than the width of the absorbent core. The tissue layer can be embossed into the absorbent core and/or adhered to the absorbent core by adhesive means.

The moisture barrier laminate is positioned adjacent the garment-facing surface of the absorbent core and the cover sheet is positioned adjacent the body-facing surface of the absorbent core. The moisture barrier sheet and cover sheet are preferably joined together by means well known in the art. For example, the moisture barrier sheet and cover sheet may be secured to each other on the peripheral edges by a uniformed continuous layer of adhesive, a pattern layer adhesive, or an array of separate lines, spirals, or spots of adhesive. Adhesives which have been found to be satisfactory are hot-melt pressure adhesives manufactured by H.B. Fuller Company, Findley Adhesives, Inc., and National Starch and Chemical Company. Alternatively, the attachment means may comprise heat bonds, pressure bonds, ultrasonic bonds, dynamic mechanical bonds, or any other suitable attachment means or combinations of these attachment means as are known in the art.

Furthermore, the cover sheet may also be affixed to the absorbent core by the above means.

The moisture barrier laminate is impervious to liquids such as urine and menses and is a multi-layered, preferably a two-layered laminate comprised of a polymeric foam layer/structure and at least one, preferably one, thermally bonded layer, e.g., a carded nonwoven material. The laminate is positioned with the polymeric foam layer adjacent the garment-facing surface of the absorbent core. The polymeric foam layer/structure and thermally bonded layer are laminated. The polymeric foam layer and thermally bonded layer may be laminated by adhering with a spray hot melt adhesive. Preferably, the polymeric foam layer has a thickness of from about 0.002 to about 0.005 inch and a tensile strength of from about 65 lbs/in$^2$(MD) to about 80 lbs/in$^2$(MD), most preferably about 73 lbs/in$^2$(MD), and from about 30 lbs/in$^2$(TD) to about 40 lbs/in$^2$(TD), most preferably about 36 lbs/in$^2$(TD). Furthermore, the polymeric foam layer of the present invention preferably has an elongation of from about 35% (MD) to about 45% (MD), most preferably, about 39% (MD), and from about 30% (TD) to about 40% (TD), most preferably about 34% (TD). In addition, the foam layer preferably has a compression strength at 10% of from about 0.2 lb/in$^2$ to about 0.6 lb/in$^2$, most preferably about 0.4 lbs/in$^2$; at 25% of from about 2.0 lbs/in$^2$ to about 2.5 lbs/in$^2$, most preferably about 2.3 lbs/in$^2$; and at 50% of from about 8.0 lbs/in$^2$ to about 9.5 lbs/in$^2$, most preferably about 8.9 lbs/in$^2$ All of these physical parameters are measured through the testing standard ASTM D3575-84. The laminate of the present invention has a flexural resistance of between about 16 grams and about 106 grams, preferably about 45 to about 75 grams. The flexural resistance is obtained with the use of a Chatillion Model Number DPP 5 instrument by testing a 37.5 mm/side square sample of the laminate. Most preferably, the polymeric foam layer/structure is polyethylene.

This laminate gives the cup-shaped absorbent article of the present invention unique characteristics as compared to existing thermoformed polyethylene shell products. The advantage of this novel approach is to be able to realize the same advantages of the "boat" or "cup" designs which are formed by the thermoforming of foams, while avoiding the costly and slow process of thermoforming. The advantage of achieving this "cup" shape design is: 1) it provides the user with a feeling of security as the article retains its shape while in use; and, 2) it provides the article with a distinct geometry which acts as a container. The flexural characteristics of the foam are a key characteristic in obtaining the ideal performance of the product. Several varieties of cross-linked polyethylene foam had been analyzed and tested with poor results. It was not until the laminate with the properties described above was prepared and tested that the absorbent article achieved its performance advantages.

The use of elastic leg gathers, much practiced in the diaper product category, in conjunction with the laminate of the present invention, lends the absorbent article its unique "cup"-like shape. Previous attempts involving "curving" the pad by a certain amount of degrees with elastomeric elements along the side of the pads have been unsatisfactory, in part, due to the angles of curvature which are low and provide little if any support for the retention of the cup shape while in use. The synergy of the retractive forces of the elastic with the flexural rigidity of the laminate of the present invention provides the absorbent article with a "cupping strength" in the range of about 30 to about 90 grams, preferably about 45 to about 65 grams. This "cupping strength" is the force required to open the absorbent article from its original folded position to a plane normal to the horizontal plane. The instrument used to measure this "cupping strength" is a modified shear adhesion tester with a Chatillion gauge. These results provide the absorbent article with the optimum performance while in use.

Figure 2:
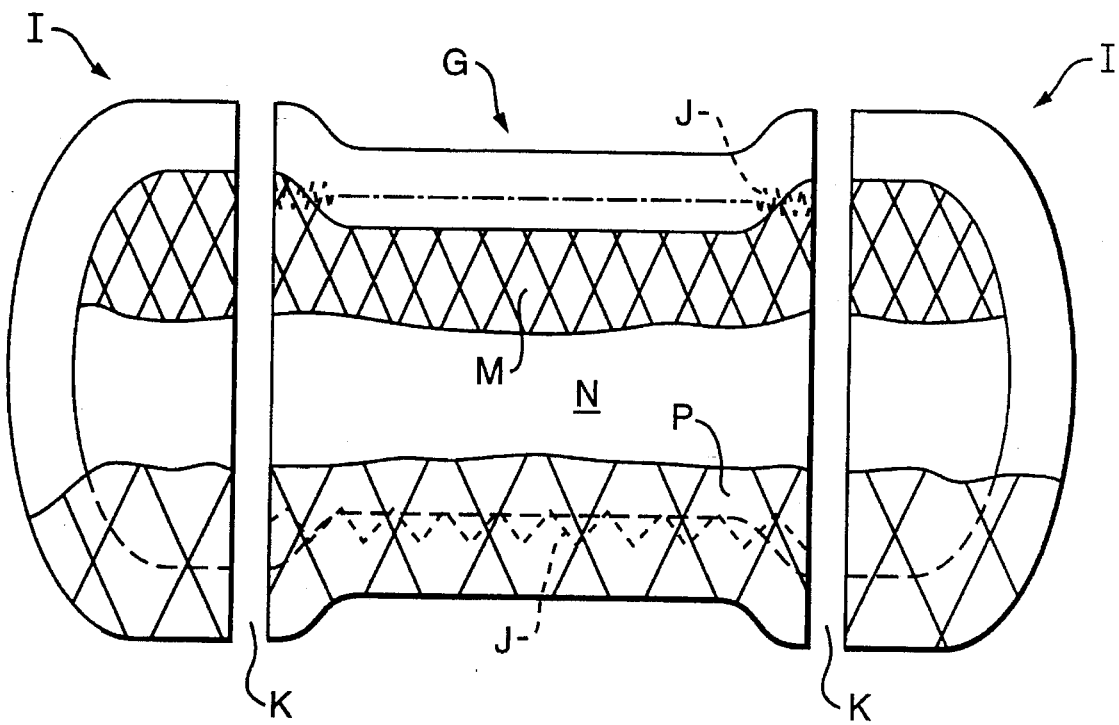
FIG. 2 is a top view of an absorbent article of the present invention, with portions cut away, to be tested for cupping strength.
Figure 3:
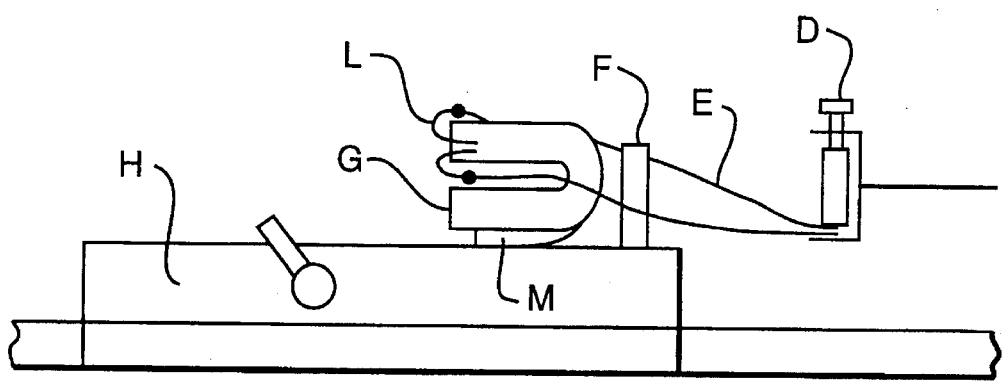
FIG. 3 is an enlarged view of the equipment for measuring the cupping strength of the absorbent article.

The test is conducted as follows:

Referring to FIGS. 1–3, a plate (F) is placed on the right side edge of and perpendicular to horizontal adhesion platform (H). An absorbent article (G) to be tested has its end portions (I) cut away (as shown in FIG. 2) at cut points (K) where the elastic members (J), e.g. leg gathers, begin.

Referring particularly now to FIG. 3, two lines (E) with hooks (L) attached at one end of each line are secured to the grasping plate (D). A Chatillion gauge (C), is located adjacent the right side of the plate (D), see FIG. 1. The cut absorbent article (G) is then placed on the platform (H) such that the two ends of the cut absorbent article (G) face away from the plate (F) and the center crotch area of the article (G) is against the plate (F). One hook (L) is attached to each top side edge of the article (G), while the surface facing the platform (H) is adhered to the platform (e.g., using the pressure sensitive adhesive means (M)). Then the hooks (L) pull the top portion of the article (G) toward the plate (F) and the amount of force (i.e., cupping strength) required to bring this top portion of the article (G) to a point which touches the plate (F) is measured.

A particularly preferred foam layer/structure is polyethylene, manufactured by Cell Aire (New Jersey) and is designated CA-30.

The size of the moisture barrier laminate as well as the cover sheet is dictated by the size of the absorbent core and the exact absorbent article shape desired. Generally, the cover sheet and moisture barrier laminate extend an optimum distance beyond the edges of the absorbent core to form extended tabs which can be sealed together using the sealing means described above.

The cover sheet is compliant, soft feeling, and not irritating to the wearer's skin. The cover sheet is fluid pervious and thus allows liquids such as menses and/or urine to readily penetrate through its thickness. For purposes of the present invention, the cover sheet may be any type of cover sheet known to those skilled in the art such as an apertured plastic film, cover sheets manufactured from porous foams, particulated foams, or woven or nonwoven webs of natural fibers (e.g., wood or cotton fibers), synthetic fibers (e.g., polyester or polypropylene fibers), or combinations of natural and synthetic fibers. In the present invention, it is preferred that the cover sheet be hydrophilic. More preferably, the cover sheet (P) (FIG. 2) is a nonwoven fluid pervious material and is embossed, preferably diamond-shaped embossed.

Though not necessary, the body-facing surface of the cover sheet can be made hydrophilic by treating it with a surfactant by techniques known to those skilled in the art such as spraying, padding, or use of transfer rolls.

Elastic members are attached to longitudinal sides of the crotch area of the article (i.e., central portion of the absorbent article) to form leg gathers. The elastic members preferably have the following physical properties: a tension of from about 120 to about 200 lbs, a denier strength of from about 740 to about 940 denier, and an elongation of from about 250% to about 300%. The elastic members can be applied on the extended tabs of the cover sheet and barrier laminate or through the cover sheet, barrier laminate, and absorbent core. Preferably, three strands of elastic (e.g., LYCRA) are applied to each extended tab side of the crotch area with, e.g., a spray hot melt adhesive to form these leg gathers. The strands of elastic are applied in the contracted state thus allowing the absorbent article and in particular, the absorbent core and barrier laminate, to form into a shape which will permit it to hold a substantial volume of liquid and also permit the article to have the cupping strength described above.

Optionally, one wide line of pressure sensitive hot melt adhesive is applied to the garment-facing side of the moisture barrier laminate. This adhesive is preferably covered with a silicone coated release paper strip which can subsequently be used to adhere the absorbent article to a garment of the user.

The present invention will be further clarified by the following example, which is intended to be purely exemplary of the present invention.

EXAMPLE 1

Figure 4:
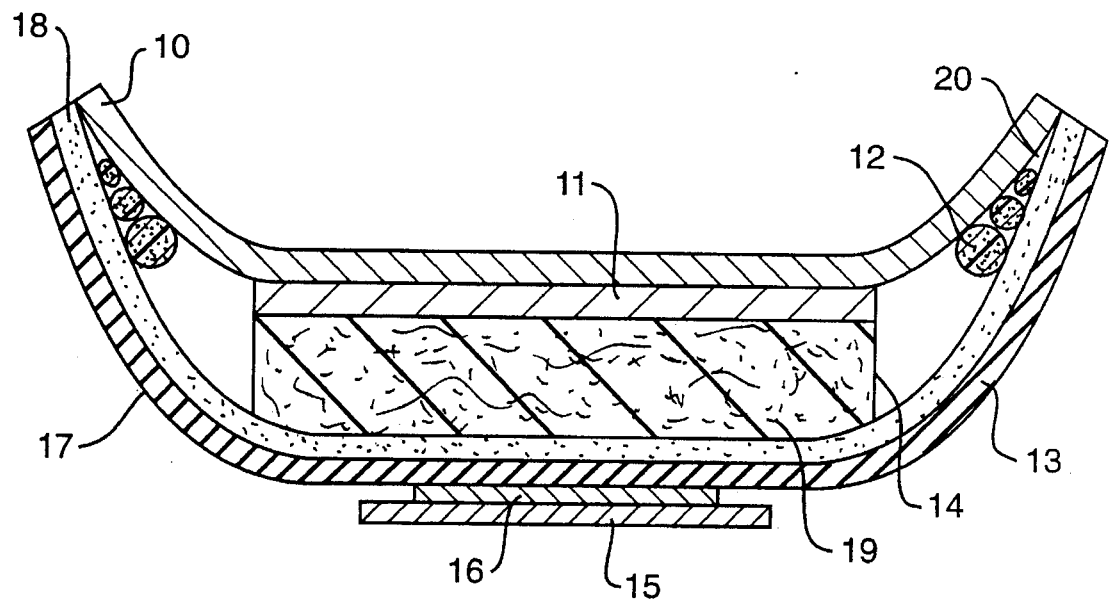
FIG. 4 is a section view of one preferred embodiment of the present invention.

A beltless urinary absorbent article as illustrated in FIG. 4, was made in the following manner. An absorbent core pad (14) of a cellulose pulp fluff was uniformly permeated with superabsorbent granules (19) of a hydrogel-forming polymer (Stockhausen Grade 800, 5.0 gm/pad). The weight of the cellulose fluff pulp was about 13.0 gm. This pad (14) of cellulose pulp fluff was then adhered by a hot melt adhesive to a blue tissue layer (11) which was embossed (diamond-shaped) into the pulp fluff of the pad (14). A moisture barrier laminate (13, 17) was prepared by laminating a polyethylene foam layer (13) obtained from Cell-Aire, CA-30, with a carded thermally bonded nonwoven material layer (17). The thickness of this laminate was 0.003 to 0.005 inch. Then, the garment-facing surface of pad (14) was adhered to the moisture barrier laminate using the same hot melt adhesive as above.

The nonwoven material layer (17) laminated to the polyethylene foam layer (13) gives the perception that the overall absorbent article is cloth-like which is pleasing to the user.

Then, a nonwoven material cover sheet (10) which was embossed (diamond-shaped) was adhered to the top of the tissue layer by the same hot melt adhesive used above. The cover sheet (10) and barrier laminate (13, 17) extend beyond the absorbent core and tissue layer to form an extended tab (18) around the edges thereof. On each side of the crotch area of the article, in the area between the portion of the extended tab (18) to be sealed and the absorbent core, three strands of LYCRA elastic (12) were adhered to the moisture barrier laminate with the same hot melt adhesive used above to form leg gathers having the flexural resistance of the present invention. The extended tab (18) is then sealed via sealing means (20), the hot melt adhesive. Lastly, one wide line of hot melt adhesive (16) was applied to the garment-facing surface of the moisture barrier laminate and covered with a silicone coated release paper strip (15).

EXAMPLE 2

Figure 5:
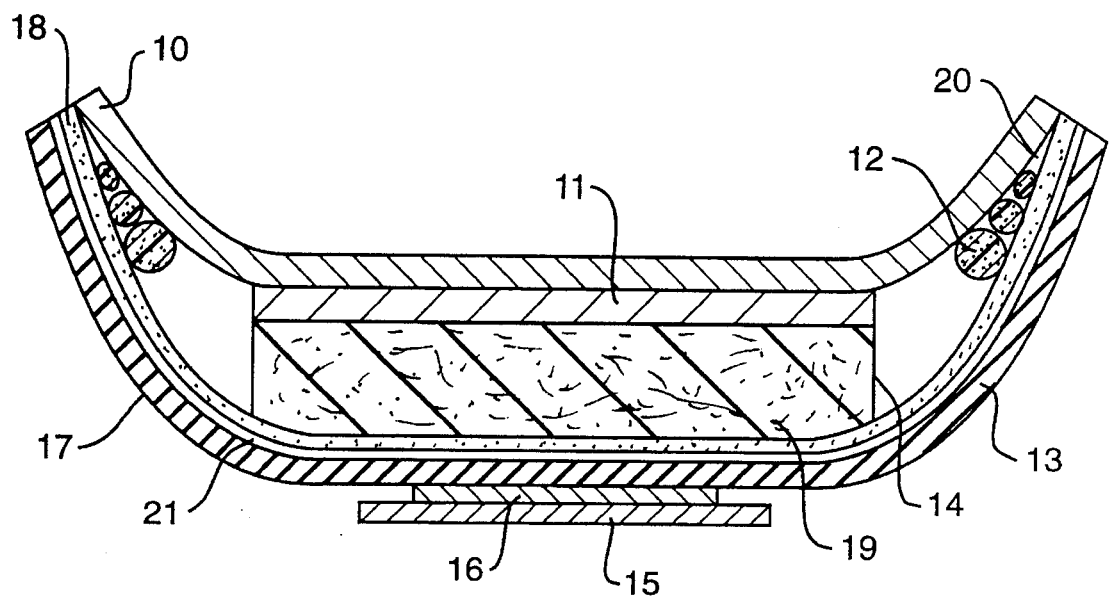
FIG. 5 is a section view of another preferred embodiment of the present invention.

FIG. 5 shows an embodiment of the present invention the same as that illustrated in FIG. 4 only the moisture barrier laminate (13,17) is prepared by adhering a polyethylene foam layer (13) with a carded thermally bonded nonwoven material layer (17) by a spray hot melt adhesive (21).

Other embodiments of the present invention will be apparent to those skilled in the art from consideration of the specification and practice of the present invention disclosed herein. It is intended that the specification and the example be considered as exemplary only, with a true scope and spirit of the present invention being indicated by the following claims.

What is claimed is:
1. An absorbent cup-shaped article comprising:
   (a) a cover sheet of a fluid pervious material;
   (b) an absorbent core permeated with a superabsorbent polymer and having a garment-facing surface and a body-facing surface;
   (c) a multi-layered moisture barrier laminate, comprised of a polymeric foam layer and at least one thermally bonded layer, wherein said laminate has a flexural resistance of from about 60 grams to about 106 grams;
   (d) said laminate is positioned with said foam layer adjacent the garment-facing surface of said absorbent core, the cover sheet is positioned adjacent the body-facing surface of said absorbent core and the cover sheet and laminate being sealed together to enclose said absorbent core; and
   (e) elastic members attached to longitudinal sides of said article to form said cup-shaped article which has a cupping strength of from about 30 grams to about 90 grams.
2. The absorbent article of claim 1 further comprising a tissue layer located on said body-facing surface.
3. The absorbent article of claim 1 wherein said cover sheet is nonwoven.
4. The absorbent article of claim 1 wherein said cover sheet is embossed.
5. The absorbent article of claim 1 wherein said cover sheet is diamond-shaped embossed.
6. The absorbent article of claim 1 wherein said absorbent core includes a contoured pulp fluff pad.
7. The absorbent article of claim 1 wherein said absorbent core is embossed.
8. The absorbent article of claim 1 wherein said superabsorbent polymer is granular.
9. The absorbent article of claim 1 wherein said absorbent core is sprayed with an odor neutralizer.
10. The absorbent article of claim 2 wherein said tissue layer extends the entire length of the absorbent core.
11. The absorbent article of claim 1 wherein said polymeric foam is a polyethylene foam.
12. The absorbent article of claim 1, wherein said thermally bonded layer is a nonwoven material.
13. The absorbent article of claim 1 wherein said polymeric foam and thermally bonded layer are adhered with a spray hot melt adhesive.
14. The absorbent article of claim 1 having the shape of a dumbbell.
15. The absorbent article of claim 1 wherein said cover sheet and said moisture barrier laminate extend beyond the absorbent core to form extended tabs thereof.
16. The absorbent article of claim 15, wherein said extended tabs are sealed together by sealing means.
17. The absorbent article of claim 1, wherein said absorbent article is an incontinence pad.
18. The absorbent article of claim 1, wherein said laminate has a flexural resistance of from about 45 to about 70 grams.
19. The absorbent article of claim 1, wherein said elastic members are elastic strands.
20. The absorbent article of claim 1, wherein said cupping strength is from about 45 to about 65 grams.

* * * * *